United States Patent
Eaton

(10) Patent No.: US 9,901,716 B2
(45) Date of Patent: Feb. 27, 2018

(54) TIPLESS BALLOON CATHETER WITH STIFFENING MEMBER THROUGH BALLOON

(71) Applicant: Cook Medical Technologies LLC, Bloomington, IN (US)

(72) Inventor: Elizabeth A. Eaton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 781 days.

(21) Appl. No.: 14/298,086

(22) Filed: Jun. 6, 2014

(65) Prior Publication Data

US 2015/0073467 A1  Mar. 12, 2015

Related U.S. Application Data

(60) Provisional application No. 61/875,789, filed on Sep. 10, 2013.

(51) Int. Cl.
*A61M 25/10* (2013.01)
*A61M 25/00* (2006.01)

(52) U.S. Cl.
CPC .......... *A61M 25/10* (2013.01); *A61M 25/0075* (2013.01); *A61M 2025/0059* (2013.01); *A61M 2025/1084* (2013.01); *A61M 2025/1093* (2013.01)

(58) Field of Classification Search
CPC .............. A61M 25/10; A61M 25/0075; A61M 2025/1063; A61M 2025/1093; A61M 2025/0059
See application file for complete search history.

(56) References Cited

U.S. PATENT DOCUMENTS

| | | | |
|---|---|---|---|
| 4,983,167 A | | 1/1991 | Sahota |
| 5,181,921 A | * | 1/1993 | Makita .............. A61B 17/12109 604/247 |
| 5,318,529 A | * | 6/1994 | Kontos ............... A61M 25/104 604/103.1 |
| 5,364,354 A | * | 11/1994 | Walker .................... A61L 29/04 604/103.1 |

(Continued)

FOREIGN PATENT DOCUMENTS

| | | |
|---|---|---|
| WO | 9744084 | 11/1997 |
| WO | 2005032642 | 4/2005 |

OTHER PUBLICATIONS

Gaos, Coronado, Edelman and Angelini; The Probe: a Balloon-on-the-Wire; Texas Heart Institute Journal; pp. 95-101; Houston, Texas.

*Primary Examiner* — Katherine Rodjom
(74) *Attorney, Agent, or Firm* — Liell + McNeil

(57) ABSTRACT

A tipless balloon catheter includes an elongate tubular body defining an inflation lumen and having proximal and distal ends. A balloon has a proximal neck mounted on the distal end of the elongate tubular body and a distal neck including a distal tip having a distal opening therethrough. The distal opening is in fluid communication with the inflation lumen and an interior of the balloon. A stiffening member extends between the distal end of the elongate tubular body and the distal neck of the balloon. The tipless balloon catheter has a wire guide path defined by the elongate tubular body, the interior of the balloon, and the distal opening.

20 Claims, 2 Drawing Sheets

(56) References Cited

U.S. PATENT DOCUMENTS

| | | | |
|---|---|---|---|
| 5,458,639 A | | 10/1995 | Tsukashima et al. |
| 5,716,373 A | * | 2/1998 | Wolvek ............... A61M 1/1072 606/191 |
| 5,766,192 A | | 6/1998 | Zacca |
| 5,776,099 A | * | 7/1998 | Tremulis ............... A61M 25/10 604/96.01 |
| 6,322,534 B1 | | 11/2001 | Shkolnik |
| 6,475,187 B1 | | 11/2002 | Gerberding |
| 6,656,153 B1 | * | 12/2003 | Sakai ................ A61M 25/0075 604/164.13 |
| 2003/0028127 A1 | * | 2/2003 | Balzum ............. A61M 25/0905 600/585 |
| 2003/0032974 A1 | | 2/2003 | Leschinsky et al. |
| 2003/0125761 A1 | | 7/2003 | Meens et al. |
| 2003/0195545 A1 | | 10/2003 | Hermann et al. |
| 2004/0116852 A1 | | 6/2004 | Scopton |
| 2004/0236366 A1 | | 11/2004 | Kennedy, II et al. |
| 2007/0083188 A1 | * | 4/2007 | Grandt .................. A61M 25/10 604/524 |
| 2007/0250149 A1 | | 10/2007 | Von Oepen et al. |
| 2011/0213401 A1 | | 9/2011 | Grayzel et al. |
| 2012/0078096 A1 | * | 3/2012 | Krolik ............... A61B 17/22032 600/435 |
| 2012/0265229 A1 | | 10/2012 | Rottenberg et al. |

* cited by examiner

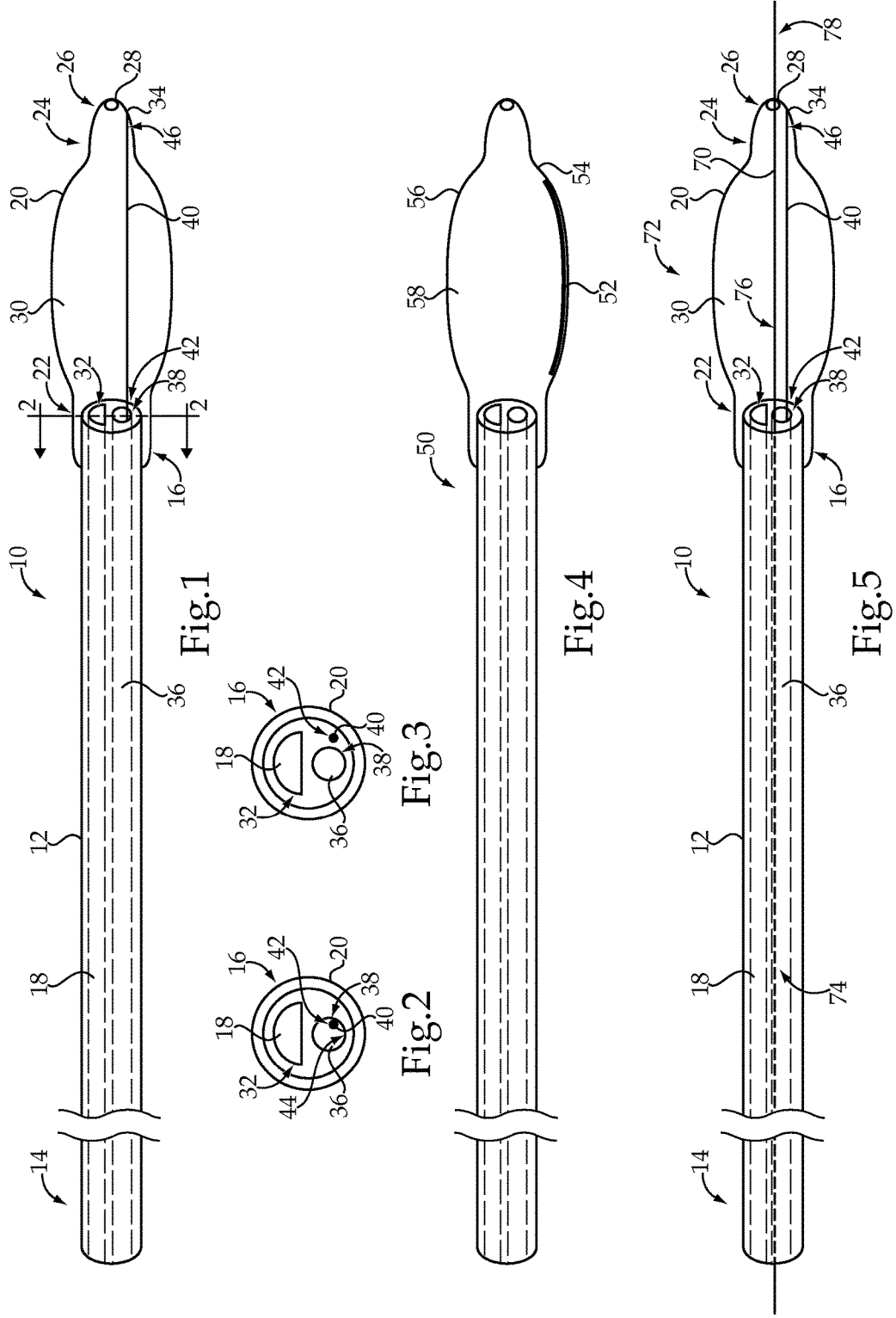

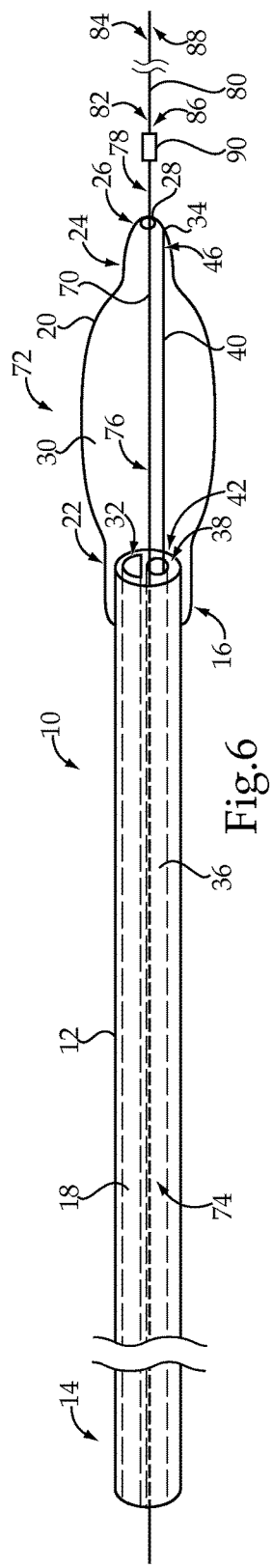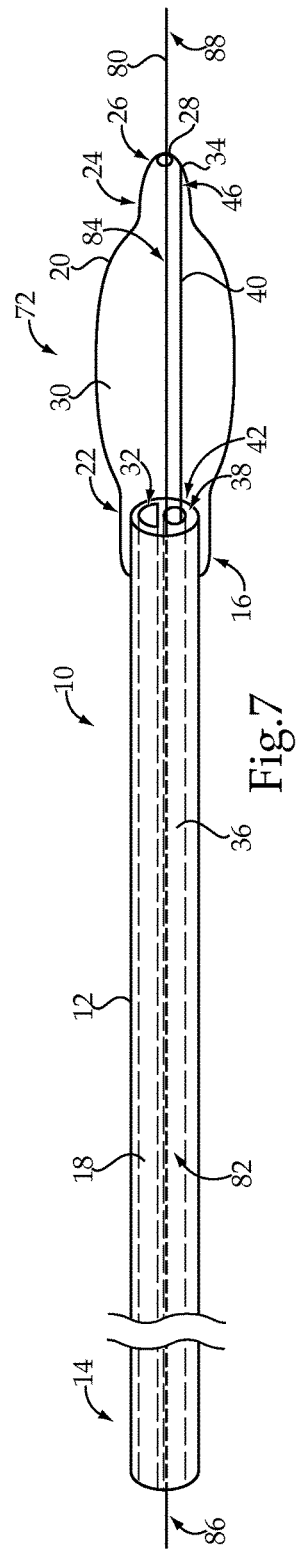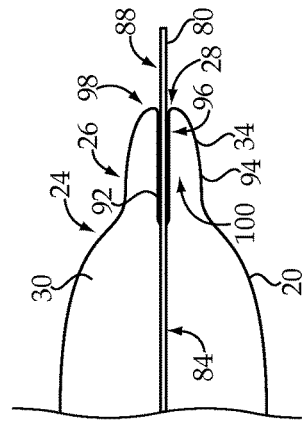

TIPLESS BALLOON CATHETER WITH STIFFENING MEMBER THROUGH BALLOON

TECHNICAL FIELD

The present disclosure relates generally to a low profile balloon catheter that does not include a continuous wire lumen passing through the balloon, and more particularly to such a low profile balloon catheter that includes a stiffening member through the balloon.

BACKGROUND

Balloon catheters include an elongate tubular body defining one or more lumens, with an inflatable balloon positioned at a distal end of the elongate tubular body. Balloon catheters provide minimally invasive means for treating various conditions. For example, angioplasty is a common procedure used to treat cardiovascular disease. During an angioplasty procedure, a medical device, such as a balloon catheter, may be percutaneously inserted, over a wire guide, into a vessel narrowed by stenosis. The balloon may be expanded at the stenosis to ultimately restore blood flow through the vessel. In some cases, a stent may be placed at the narrowed portion of the vessel, using the balloon catheter, to help keep the vessel open.

The elongate tubular body of a balloon catheter typically has multiple lumens, with one lumen being an inflation lumen for the balloon and another lumen serving as a wire guide lumen for advancing the balloon catheter over a wire guide. The elongate tubular body of one type of balloon catheter terminates just inside a proximal end of the balloon, and a smaller single lumen shaft is bonded to the distal end of the elongate tubular body and extends through to a distal end of the balloon. The single lumen shaft permits the balloon to be mounted distally and advanced over the wire guide without the wire guide scraping or puncturing the balloon. While the single lumen shaft improves pushability of the balloon catheter by increasing column strength, the presence of the single lumen shaft inside the balloon adds to the overall dimensions of the balloon. There exists a need for balloon catheters having lower profiles and, since the balloon section often represents the longest diameter of the device, decreasing the contribution of the single lumen shaft to the diameter is desirable.

SUMMARY OF THE DISCLOSURE

In one aspect, a tipless balloon catheter includes an elongate tubular body defining an inflation lumen and having proximal and distal ends. A balloon has a proximal neck mounted on the distal end of the elongate tubular body and a distal neck including a distal tip having a distal opening therethrough. The distal opening is in fluid communication with the inflation lumen and an interior of the balloon. A stiffening member extends between the distal end of the elongate tubular body and the distal neck of the balloon. The tipless balloon catheter has a wire guide path defined by the elongate tubular body, the interior of the balloon, and the distal opening.

In another aspect, a tipless balloon catheter system includes an elongate tubular body defining an inflation lumen and having proximal and distal ends. A balloon has a proximal neck mounted on the distal end of the elongate tubular body and a distal neck including a distal tip having a distal opening therethrough. The tipless balloon catheter system also includes a stiffening member extending between the distal end of the elongate tubular body and the distal neck of the balloon, and a build wire having a first portion, a second portion, and a distal end. The tipless balloon catheter system has a first configuration in which the first portion of the build wire is disposed within the elongate tubular body, the second portion of the build wire is disposed within the interior of the balloon, and the distal end of the build wire projects through the distal opening.

BRIEF DESCRIPTION OF THE DRAWINGS

FIG. 1 is a side view of a tipless balloon catheter, shown with portions of the balloon removed to show a stiffening member, according to one embodiment of the present disclosure;

FIG. 2 is a cross sectional view taken along lines 2-2 of FIG. 1;

FIG. 3 is a cross sectional view similar to that of FIG. 2, depicting an alternative attachment arrangement;

FIG. 4 is a side view of another alternative tipless balloon catheter;

FIG. 5 is a side view of a tipless balloon catheter system including the tipless balloon catheter of FIG. 1, depicting the tipless balloon catheter prior to insertion over a wire guide;

FIG. 6 is a side view of the tipless balloon catheter system of FIG. 5, depicting a build wire of the tipless balloon catheter coupled with a wire guide;

FIG. 7 is a side view of the tipless balloon catheter system of FIGS. 5 and 6, depicting the tipless balloon catheter advanced over the wire guide; and FIG. 8 is a side cutaway view of a one embodiment of a distal tip forming a seal around a wire guide.

DETAILED DESCRIPTION

Referring to FIG. 1, there is shown a tipless balloon catheter 10 according to one embodiment of the present disclosure. The tipless balloon catheter 10 generally includes an elongate tubular body 12 having a proximal end 14 and a distal end 16. The elongate tubular body 12 may be made from any common medical tube material, such as, for example, polytetrafluoroethylene (PTFE), high density polyethylene (HDPE), nylon, polyetheretherketone (PEEK), or any vinyl, plastic, rubber, or silicone, and may exhibit both stiffness, or firmness, and flexibility. Materials as well as dimensions may vary depending on the particular application. In the present disclosure, "proximal" will be used to refer to the end of a component or feature that is closest to a clinician, while "distal" is used to refer to a component or feature that is farthest away from the clinician. Such meanings are consistent with conventional use of the terms and, as such, should be understood by those skilled in the art.

The elongate tubular body 12 defines an inflation lumen 18 extending from the proximal end 14 to a balloon 20 disposed at the distal end 16 of the elongate tubular body 12. The balloon 20, which is made from common medical balloon materials, has a proximal neck 22 mounted on the distal end 16 of the elongate tubular body 12, and a distal neck 24 including a distal tip 26 having a distal opening 28 therethrough. The elongate tubular body 12 terminates in the proximal neck 22 of the balloon 20, with the inflation lumen 18 being in fluid communication with an interior 30 of the balloon 20 at opening 32. According to the exemplary embodiment of the present disclosure, the interior 30 of the balloon 20 and, thus, the inflation lumen 18 are also in fluid communication with the distal opening 28. That is, the inflation lumen 18 and the interior 30 of the balloon 20 are in fluid communication with an external environment surrounding the balloon 20 through the distal opening 28.

The proximal neck 22 of the balloon 20 may be bonded or connected to the elongate tubular body 12 at the distal end 16. For example, the proximal neck 22 may be bonded to the distal end 16 of the elongate tubular body 12 with PEEK or other similar material used to keep any lumens, such as the inflation lumen 18, open during the bonding process. According to some embodiments, the distal neck 24 of the balloon 20 may be bonded to a soft tip 34. The soft tip 34 may be separate from or integral with the balloon 20, and may define an atraumatic soft tip of the tipless balloon catheter 10. The soft tip 34, whether integral with or separate from the balloon 20, may define the distal opening 28.

The elongate tubular body 12 may also define a wire guide lumen 36 extending from the proximal end 14 to the distal end 16 of the elongate tubular body 12. The wire guide lumen 36 and the inflation lumen 18 may terminate near each other at the distal end 16 of the elongate tubular body 12, which terminates within or near to the proximal neck 22 of the balloon 20. Thus, the wire guide lumen 36 may also be in fluid communication with the interior 30 of the balloon 20 through opening 38. In addition to other uses, including additional uses described below, the wire guide lumen 36 may be used to advance the tipless balloon catheter 10 over a wire guide. Although two lumens 18, 36 are shown in the exemplary embodiment, the present disclosure is applicable to single lumen devices and devices having more than two lumens. Multiple lumens may be provided in a side-by-side configuration, a coaxial configuration, or other known configurations, and may have any of a variety of known cross-sectional shapes.

The "tipless" balloon catheter 10, as described herein, lacks an internal shaft or cannula through the interior 30 of the balloon 20. That is, there is not a shaft or cannula, such as a wire guide shaft or cannula, for supporting a device, such as a wire guide, as it is passed through the interior 30 of the balloon 20. The tipless balloon catheter 10 may still include the soft tip 34 described above and be considered "tipless." The absence of a shaft or cannula within the balloon 20 gives the balloon 20 a lower profile and greater flexibility, particularly when compared to conventional balloon catheters that include a wire guide shaft. For example, conventional balloon catheters typically include a single lumen shaft bonded to the distal end 16 of the elongate tubular body 12 and extending through to a distal portion of the balloon 20. The bulk of the single lumen shaft, in addition to the bulk of the balloon materials, adds significantly to the profile of the device.

The tipless balloon catheter 10 of the present disclosure includes a stiffening member 40 extending at least between the distal end 16 of the elongate tubular body 12 and the distal neck 24 of the balloon 20. The stiffening member 40 may include any metallic or non-metallic wire, string, thread, cable, cord, chain, fiber, etc. capable of increasing column strength and/or pushability of the tipless balloon catheter 10 at the region of the balloon 20 without increasing profile as much as would a single lumen tip material. The stiffening member 40 compensates for the decrease in column strength resulting from the absence of a shaft or lumen through the interior 30 of the balloon 20 and may have a size and configuration selected to perform the functionality described herein.

The stiffening member 40 may be solid or hollow or pattern-cut as a single tube or rod with laser lines to give it flexibility, and may be made from any of a number of materials. For example, the stiffening member 40 may be made from stainless steel, nitinol, cobalt chrome, or other metal, or a plastic. The stiffening member 40 may have any desired length and placement. For example, the stiffening member 40 may extend a majority or the entirety of a length of the tipless balloon catheter 10, or may just extend from the distal end 16 of the elongate tubular body 12 to the distal neck 24 of the balloon 20. The stiffening member 40 may be movable with respect to the elongate tubular body 12 or may be stationary relative to the elongate tubular body 12. According to a first exemplary embodiment, shown in FIG. 1, the stiffening member 40 extends through the interior 30 of the balloon 20, directly contacting any fluid provided within the balloon 20, and includes a proximal end 42 that is attached to the distal end 16 of the elongate tubular body 12.

Specifically, as shown in FIG. 2, the proximal end 42 of the stiffening member 40 may be attached to an inner wall 44 defining the wire guide lumen 36. For example, the proximal end 42 of the stiffening member 40 may be welded, glued, or otherwise bonded, affixed, or adhered, to the inner wall 44. Although the proximal end 42 of the stiffening member 40 is shown attached within the wire guide lumen 36, the stiffening member 40 may alternatively be attached within the inflation lumen 18 or any other lumen that is provided. Alternatively, as shown in FIG. 3, the proximal end 42 of the stiffening member 40 may be attached to or formed integrally with the elongate tubular body 12 and may be spaced apart from both of the inflation lumen 18 and the wire guide lumen 36. According to the latter embodiment, manufacturing may be eased if the stiffening member 40 also runs the entire length of the elongate tubular body 12. According to either embodiment, a distal end 46 of the stiffening member 40 may be attached to the distal tip 26 of the balloon 20. For example, the distal end 46 may be welded, bonded, or otherwise affixed to the soft tip 34.

According to another alternative embodiment, shown in FIG. 4, a tipless balloon catheter 50, similar to the tipless balloon catheter 10 described above, may include a stiffening member 52 supported within a wall 54 of a balloon 56. The stiffening member 52 may be similar with respect to materials and configuration to the stiffening member 40 described above but, rather than extending through a balloon interior 58, the stiffening member 52 may be adhered to or embedded within the balloon wall 54. Depending on the means for attaching the stiffening member 52 to the balloon wall 54, the stiffening member 52 may or may not directly contact any fluid provided within the balloon 56. Although one stiffening member 40 or 52 is shown in the exemplary embodiments, additional stiffening members may be used. Further, the one or more stiffening members, including stiffening members 40 and 52, may be continuous or discontinuous along a longitudinal axis of the device.

According to these embodiments, and others, the stiffening member 40, 52 of the present disclosure will typically be smaller than the single lumen shaft provided in conventional balloon catheter "tips." According to some conventional balloon catheters, a typical tip, which includes a single lumen wire guide shaft, might have an outer diameter of 0.050 inch and an inner diameter sufficient to pass a 0.035 inch wire guide. According to an exemplary embodiment of the present disclosure, the 0.050 inch tip may be replaced with a stiffening member 40, 52 of approximately 0.020 inch and a wire guide of approximately 0.014 inch. That is, a smaller and more flexible wire guide may be selected since the stiffening member 40, 52 will provide some of the needed column strength. While the dimensions are provided for exemplary purposes only, it should be appreciated that, according to the example, a total thickness of approximately 0.034 inch, including the stiffening member 40, 52 and wire guide, may be substituted for the previous thickness of approximately 0.050 inch.

Reference will again be made to the embodiment of FIG. 1. To effect use, and manufacture, of the tipless balloon catheter 10, a build wire 70 may be provided as part of a tipless balloon catheter system 72, as shown in FIG. 5. For example, the build wire 70 may be provided during manufacture and may include a first portion 74, a second portion 76, and a distal end 78. According to a first configuration of the tipless balloon catheter system 72, the first portion 74 of the build wire 70 is disposed within the elongate tubular body 12, the second portion 76 of the build wire 70 is disposed within the interior 30 of the balloon 20, and the distal end 78 of the build wire 70 projects through the distal opening 28. The build wire 70 may include any metallic or non-metallic wire, string, thread, cable, cord, chain, fiber, etc. capable of being positioned as described above, and capable of being exchanged for a wire guide or another build wire. The term build wire, as used herein, refers to any of the foregoing structures from which the tipless balloon catheter 10 may be advanced onto another wire, such as a wire guide that has been disposed within a patient.

The tipless balloon catheter system 72 may also include a wire guide 80, as shown in FIG. 6. The wire guide 80 may be of standard design and generally includes a first portion 82, a second portion 84, a proximal end 86, and a distal end 88. In the first configuration, described above, the distal end 78 of the build wire 70 may be coupled with the proximal end 86 of the wire guide 80 in a releasable engagement. The releasable engagement may incorporate the use of a separate structural element 90 or may include a direct connection between the distal end 78 of the build wire 70 and the proximal end 86 of the wire guide 80. With the build wire 70 and wire guide 80 coupled, the tipless balloon catheter system 72 may be transitioned to a second configuration, shown in FIG. 7, in which the first portion 82 of the wire guide 80 is disposed within the elongate tubular body 12, the second portion 84 of the wire guide 80 is disposed within the interior 30 of the balloon 20, and the distal end 88 of the wire guide 80 projects through the distal opening 28. As will be described below, the build wire 70 may be proximally retracted or withdrawn to safely guide the wire guide 80 through the balloon 20 as the tipless balloon catheter 10 is advanced over the wire guide 80.

Turning now to FIG. 8, the distal tip 26, and/or soft tip 34, of the balloon 20 (shown with the stiffening wire removed) may be configured to provide a sealing engagement around the wire guide 80, in the second configuration of the tipless balloon catheter system 72. In particular, a desirable inflation medium may be advanced through the inflation lumen 18 and into the interior 30 of the balloon 20. The fluid may transition the balloon 20 from a collapsed state to an expanded state, as shown. To prevent leakage of the fluid through the distal opening 28, the distal tip 26 may form a sealing engagement around the wire guide 80. According to one example, the distal tip 26 may have an inner sleeve 92 and an outer tubing 94, with a distal end 96 of the inner sleeve 92 and a distal end 98 of the outer tubing 94 being integral with one another or attached together. The inner sleeve 92 and outer tubing 94 may define an annular cavity 100 that is in fluid communication with the interior 30 of the balloon 20. Fluid supplied to the interior 30 of the balloon 20 may fill the annular cavity 100, with fluid pressure providing a sealing force to seal the inner sleeve 92 against the wire guide 80 and, thus, reduce or prevent leakage. Although a specific sealing arrangement is shown, it should be appreciated that the present disclosure may incorporate additional or alternative sealing arrangements for reducing fluid leakage around the wire guide 80 through the distal opening 28.

INDUSTRIAL APPLICABILITY

Referring generally to FIGS. 1-8, the tipless balloon catheter system 72 may be used in a percutaneous endovascular procedure. According to such a procedure, a clinician may first achieve access and correct position inside the patient using the wire guide 80. Next, with the tipless balloon catheter system 72 in the first configuration, the distal end 78 of the build wire 70 may be coupled to the proximal end 86 of the wire guide 80. The tipless balloon catheter 10 may then be transitioned from the build wire 70 to the wire guide 80 by distally advancing the tipless balloon catheter 10 while maintaining a relatively stationary position of the build wire 70. The build wire 70 effectively guides the wire guide 80 as the tipless balloon catheter 10 is loaded over the releasable engagement of the build wire 70 to the wire guide 80 and onto the wire guide 80. This helps reduce the risk of the proximal end 86 of the wire guide 80 damaging the balloon 20 during advancement of the tipless balloon catheter 10. Once the tipless balloon catheter 10 has been fully deployed onto the wire guide 80, the build wire 70 may be disconnected and removed.

In the second configuration of the tipless balloon catheter system 72, the first portion 82 of the wire guide 80 is disposed within the elongate tubular body 12, the second portion 84 of the wire guide 80 is disposed within the interior 30 of the balloon 20, and the distal end 88 of the wire guide 80 projects through the distal opening 28. With the tipless balloon catheter system 72 in the second configuration and properly positioned within the patient, an inflation medium may be advanced through the inflation lumen 18 and into the interior 30 of the balloon 20 to expand the balloon 20. To prevent leakage of the fluid through the distal opening 28, the distal tip 26 may form a sealing engagement around the wire guide 80, as described above.

The tipless balloon catheter system 72 of the present disclosure includes the tipless balloon catheter 10 described herein, which has a lower profile than conventional balloon catheters. In particular, the tipless balloon catheter 72 lacks a shaft or cannula, such as a wire guide shaft, within the balloon 20, thus resulting in the lower profile. The method for advancing the tipless balloon catheter 10, which uses the build wire 70 and a releasable engagement between the build wire 70 and the wire guide 80, provides for atraumatic advancement of the tipless balloon catheter 72 over the wire guide 80 in spite of the absence of a wire guide shaft through the balloon 20. The tipless balloon catheter system 72 also includes a stiffening member 40, which might run in parallel with the build wire 70 and wire guide 80.

The stiffening member 40 extends at least between the distal end 16 of the elongate tubular body 12 and the distal neck 24 of the balloon 20. The stiffening member 40 may increase column strength and/or pushability of the tipless balloon catheter 10 at the region of the balloon 20 without increasing profile as much as would a wire guide lumen. The stiffening member 40 compensates for the decrease in column strength resulting from the absence of a shaft or lumen through the interior 30 of the balloon 20. Due to the incorporation of the stiffening member 40, the clinician may be able to use a smaller or more flexible wire guide than would otherwise be selected, knowing that the stiffening member 40 will compensate for some of the needed column strength. The stiffening member 40 also provides structure at the balloon region that may ease manufacturing of the tipless balloon catheter 10 and help reduce buckling during manufacture and/or use.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A tipless balloon catheter, comprising:
   an elongate tubular body defining an inflation lumen and having proximal and distal ends;
   a balloon having a proximal neck mounted on the distal end of the elongate tubular body and a distal neck including a distal tip having a distal opening therethrough, wherein the distal opening is in fluid communication with the inflation lumen and an interior of the balloon;
   a stiffening member attached to the balloon and extending between the distal end of the elongate tubular body and the distal neck of the balloon;
   a wire guide path defined by the elongate tubular body, the interior of the balloon, and the distal opening;
   the stiffening member having a profile perpendicular to a longitudinal axis of the elongate tubular body that is smaller than a profile of the wire guide path defined by the elongate tubular body; and
   the distal tip of the balloon includes an inner sleeve, which defines a segment of the wire guide path, attached to an outer tubing, and wherein the inner sleeve and the outer tubing define an annular cavity that surrounds the segment and is in fluid communication with the interior of the balloon.

2. The tipless balloon catheter of claim 1, wherein the stiffening member extends through the interior of the balloon from the distal end of the elongate tubular body to the distal neck of the balloon.

3. The tipless balloon catheter of claim 1, wherein the stiffening member is supported within a wall of the balloon.

4. The tipless balloon catheter of claim 1, wherein the stiffening member has a column strengthening connection to the balloon parallel to, but offset from, the longitudinal axis of the elongate tubular body.

5. The tipless balloon catheter of claim 4, wherein the stiffening member is stationary with respect to the elongate tubular body, and a proximal end of the stiffening member is attached to the distal end of the elongate tubular body.

6. The tipless balloon catheter of claim 5, wherein the proximal end of the stiffening member is attached to an inner wall defining one of the inflation lumen and the wire guide lumen.

7. The tipless balloon catheter of claim 5, wherein the proximal end of the stiffening member is attached to the elongate tubular body and spaced apart from both of the inflation lumen and the wire guide lumen.

8. The tipless balloon catheter of claim 5, wherein a distal end of the stiffening member is attached to the distal tip of the balloon.

9. The tipless balloon catheter of claim 5, wherein the stiffening member is solid.

10. A tipless balloon catheter system, comprising:
    an elongate tubular body defining an inflation lumen and having proximal and distal ends;
    a balloon having a proximal neck mounted on the distal end of the elongate tubular body and a distal neck including a distal tip having a distal opening therethrough;
    a stiffening member extending between the distal end of the elongate tubular body and the distal neck of the balloon;
    a build wire having a first portion, a second portion, and a distal end;
    wherein the tipless balloon catheter system has a first configuration in which the first portion of the build wire is disposed within the elongate tubular body, the second portion of the build wire is disposed within the interior of the balloon, and the distal end of the build wire projects through the distal opening;
    the stiffening member having a profile perpendicular to a longitudinal axis of the elongate tubular body that is smaller than a profile of a wire guide path defined by the elongate tubular body; and
    the distal tip of the balloon includes an inner sleeve, which defines a segment of the wire guide path, attached to an outer tubing, and wherein the inner sleeve and the outer tubing define an annular cavity that surrounds the segment and is in fluid communication with the interior of the balloon.

11. The tipless balloon catheter system of claim 10, wherein the distal opening is in fluid communication with the inflation lumen and an interior of the balloon.

12. The tipless balloon catheter system of claim 11, further including a wire guide having a first portion, a second portion, a proximal end, and a distal end, wherein, in the first configuration, the distal end of the build wire is coupled coaxially with the proximal end of the wire guide.

13. The tipless balloon catheter system of claim 12, wherein the tipless balloon catheter system has a second configuration in which the first portion of the wire guide is disposed within the elongate tubular body, the second portion of the wire guide is disposed within the interior of the balloon, and the distal end of the wire guide projects through the distal opening.

14. The tipless balloon catheter system of claim 13, wherein, in an expanded position of the balloon, the distal tip of the balloon forms a sealing engagement around the wire guide responsive to fluid pressure within the balloon.

15. The tipless balloon catheter system of claim 13, wherein
    the stiffening member has a column strengthening connection to the balloon parallel to, but offset from, a longitudinal axis of the elongate tubular body.

16. The tipless balloon catheter system of claim 15, wherein the stiffening member is stationary with respect to the elongate tubular body, and a proximal end of the stiffening member is attached to the distal end of the elongate tubular body.

17. The tipless balloon catheter system of claim 16, wherein the proximal end of the stiffening member is attached to an inner wall defining one of the inflation lumen and the wire guide lumen.

18. The tipless balloon catheter system of claim 16, wherein the proximal end of the stiffening member is attached to the elongate tubular body and spaced apart from both of the inflation lumen and the wire guide lumen.

19. The tipless balloon catheter system of claim 16, wherein a distal end of the stiffening member is attached to the distal tip of the balloon.

20. The tipless balloon catheter system of claim 19, wherein the stiffening member is solid with a longitudinal axis that is parallel to the longitudinal axis of the elongate tubular body.

\* \* \* \* \*